United States Patent
Anderson-Fignon

[11] Patent Number: 5,728,137
[45] Date of Patent: Mar. 17, 1998

[54] LIQUID DISPENSING SYSTEM

[76] Inventor: Karen Anderson-Fignon, 26 Pleasant St., Woodbury, Conn. 06798

[21] Appl. No.: 683,207

[22] Filed: Jul. 18, 1996

[51] Int. Cl.⁶ ............................................. A61J 17/00
[52] U.S. Cl. .............................. 606/234; 606/236; 604/77
[58] Field of Search .......................... 606/234, 236; 604/77

[56] References Cited

U.S. PATENT DOCUMENTS

| | | | |
|---|---|---|---|
| 5,123,915 | 6/1992 | Miller et al. | 606/234 |
| 5,176,705 | 1/1993 | Noble | 606/236 |
| 5,354,274 | 10/1994 | Demeter et al. | 606/234 |
| 5,366,481 | 11/1994 | Zade | 606/236 |
| 5,578,004 | 11/1996 | Liang | 606/236 |
| 5,620,462 | 4/1997 | Valenti | 606/234 |

*Primary Examiner*—Gary Jackson
*Attorney, Agent, or Firm*—Lawrence Hager

[57] ABSTRACT

A liquid dispensing device which allows oral ingestion of a liquid at a desired or controlled rate to, for example, an infant. A holder is provided to enable the placement of the dispenser during periods when dispensing and/or feeding is interrupted or suspended. The dispenser basically comprises a transparent or semi-transparent flexible rubber like elongated cylinder having measurement markings on or about the peripheral surface. An upper flange member supports the dispenser in an upright position when placed in the holder unit. A cap is provided having means for controlling the fluid flow rate. A fluid flow blocking means is provided at the bottom of the holder unit.

14 Claims, 5 Drawing Sheets

LIQUID DISPENSING SYSTEM

FIELD OF THE INVENTION

The present invention relates to a new and improved liquid dispensing system and, more particularly, to a multi-purpose liquid dispensing and/or feeding and/or medicine delivery system to facilitate not only dosage, but also the rate of delivery to the infant.

BACKGROUND OF THE INVENTION

Typically, liquid-dispensing pacifier like devices have been used for oral administration. Parents and nurses are frequently frustrated by the task of administering such liquids to infants, toddlers and other persons requiring such feeding or dosing method. The heretofore devices are not well-suited to the general and varied applications required for the daily administration of both liquid nutrient and/or medication. For example, the prior art devices do not enable the easy and constant monitoring of the dosage or liquid consumption rate. The prior art devices also do not enable the adjustment of the flow rate to provide a controlled dosage over a period of time. And the prior art devices do not enable or provide for the temporary removal of the pacifier device with fast, convenience stopping of the liquid leakage-flow to facilitate the infants other needs such as, for example, diaper replacement or burping.

Some prior art liquid dispensing pacifier devices included a sealed cartridge which is pierced to enable liquid flow and is then placed in a device having a nipple such as is described in U.S. Pat. No. 5,354,274 issued Oct. 11, 1994 to Robert J. Demeter, et al. In total contrast to the present invention, the '274 patent does not show or suggest a device to measure the mixing, for example, of a medication dosage with a host liquid such as juice or milk, and the '274 patent does not enable fluid rate control and monitoring or convenient and fast holder means.

Another prior art patent of interest is U.S. Pat. No. 5,123,915 issued Jun. 23, 1992 to Lawrence E. Miller. This patent describes a medicated pacifier having a discrete reservoir chamber 112 formed, for example, of a hard plastic onto which a discrete nipple 116 is secured. A pill or cartridge like medication dosage is placed into the reservoir chamber.

Other prior art references include, but are not limited to, Barnes U.S. Pat. No. 404,950; Spencer U.S. Pat. No. 745,920; Baer U.S. Pat. No. 4,192,307; Connelly U.S. Pat. No. 4,488,551; White U.S. Pat. No. 4,784,641; Martin U.S. Pat. No. 5,129,532 and Mailot U.S. Pat. No. 5,127,903.

SUMMARY OF THE INVENTION

Generally, speaking, and in accordance with the invention, a liquid medication and/or nutrient measuring and dispensing system is provided having particular utility for pediatric and infant medicine and nutrient dispensing, in combination, comprising:

- a unitary elongated cylinder shaped container or reservoir chamber means having a plurality of circumferential measurement marking or indicia, and having a lower tapered section forming a nipple-like end portion, and having an open end portion, and being formed from a flexible resin or plastic like transparent or translucent material to enable viewing of a fluid level within said reservoir chamber means;
- a circular or oval shaped disc like member affixed to the upper ridge portions of said container means to form a fluid-tight seal therebetween, said disc member having a size and shape to provide the dual function of a mounting plate and a mouth guard, and having a threaded neck like member;
- a cap means having a valve member for enabling the controlled rate of air seepage into the reservoir chamber or cavity to thereby control the fluid flow rate from the opening in the nipple;
- a cradle or holder means having a base plate dimensioned for providing a stable support, said base plate includes a surface designed to engage with and depress the end portion of the nipple to provide a sealing or closing effect to the nipple opening with the dispenser being placed in cradle, a circular transparent plastic or glass container having an internal cavity for receiving said reservoir chamber means therein, and a top rim portion dimensioned for supporting said disc member thereon.

OBJECTS OF THE INVENTION

Accordingly, it is a primary object of the present invention to provide a new and improved liquid dispensing device for the administration of oral medicine and/or nutrients and/or fluids at a more controllable rate of flow to an infant.

It is yet a further object of this invention to provide a unitary liquid reservoir and nipple means.

Another object of this invention is to provide a reservoir means having measuring indicia for facilitating the desired amount or dosage of a medicine or fluid to an infant.

Another object of this invention is to provide a holder means for holding the dispenser during non-feeding periods.

Another object of this invention is to provide a means to facilitate the temporary cessation of dispensing without spilling the fluid or medication on undesired surfaces such as furniture, etc.

Another object of this invention is to provide a warming container for the fluid within the dispensing device.

Another object of this invention is to provide a virtual turnoff valve to enable the stopping of the fluid flow from the dispensing device without requiring the removal of the nipple section from the infant's mouth.

Another object of the present invention is to facilitate the mixing of various fluids and medicines at measured amounts directly within the dispensing device.

Yet another object of the present invention is to provide a liquid dispenser having a design and shape to enable it to be hand held by an infant or toddler.

And another object of the present invention is to provide a fluid flow stoppage means such that the fluid is trapped within the reservoir chamber even when the valve means is not shut off, for example, in the event the mother or nurse inadvertently forgets to shut off the valve means when burping the infant.

Another object of the present invention is to provide a multi-function cradle means for providing storage to the dispenser device, a clean environment for the nipple, a fluid chamber for maintaining the dispenser device at a selected temperature and for stopping fluid out flow from the dispenser unit.

BRIEF DESCRIPTION OF THE DRAWINGS

Other objects and advantages of the present invention will be more clearly seen when viewed in conjunction with the accompanying drawings. Like numerals refer to like parts throughout.

DETAILED DESCRIPTION OF THE INVENTION

Figure 1:
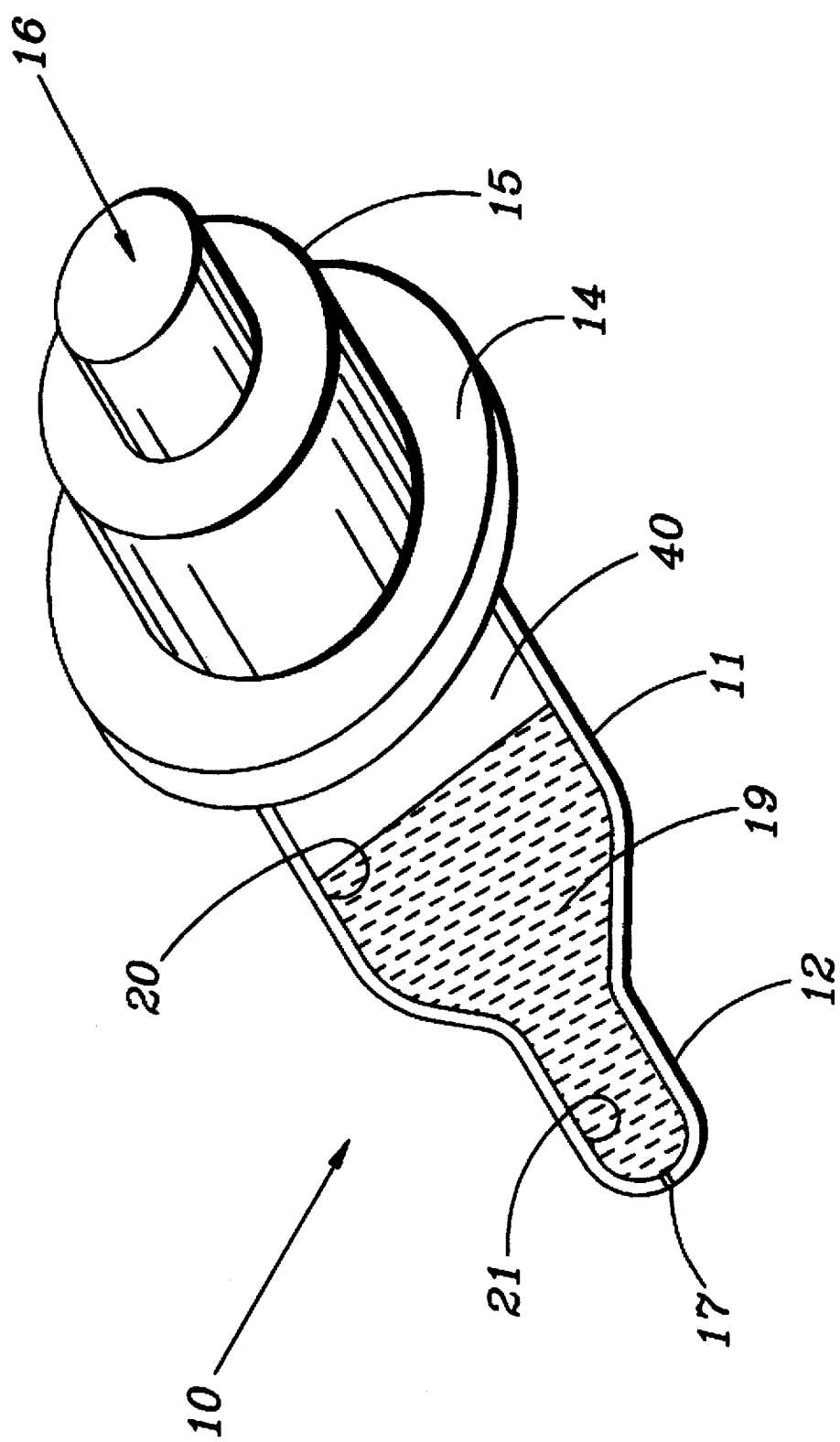
FIG. 1 is a perspective view of the liquid dispenser in accordance with the present invention.
Figure 2:
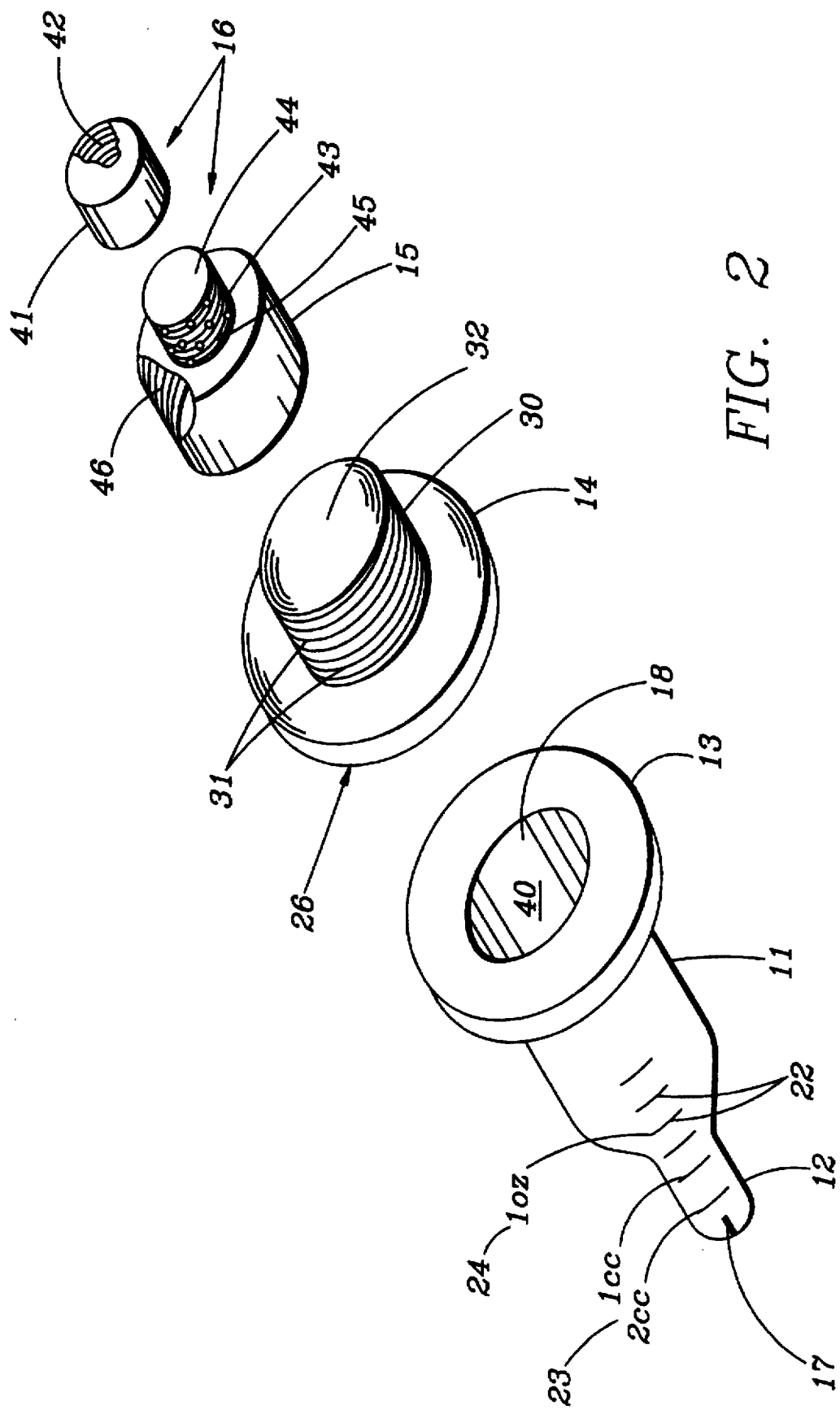
FIG. 2 is an exploded view of the dispenser illustrated in FIG. 1.

Referring now to FIGS. 1 and 2 of the drawings, a new and improved liquid dispenser 10 in accordance with a preferred embodiment of the invention is illustrated. Briefly stated, the dispenser 10 comprises a main body portion 11, a nipple section 12, an upper flange or rim member 13, a mouth guard ring and holder cover 14, an upper cap 15 and a valve member 16.

The main body portion 11 and nipple section 12 may be integrally formed of any suitable material such as, for example, a flexible latex rubber like material. The end of the nipple section 12 is provided with one or more apertures or holes 17 which extend through the nipple rubber like material into the inner fluid reservoir chamber 40. The main body portion 11 and preferably also the nipple section 12 are formed of semitransparent or opaque material to enable a person to visually determine the level or amount of fluid and/or medication 19 within the nipple 12 and main body portion 11 of dispenser 10. Preferably, the annular side wall 20 of main body portion 11 is made or molded to be thicker and more rigid than nipple section 12 which has an axially inwardly converging conical annular wall 21.

In this manner, a desired rigidity is incorporated into the main body portion 11 to facilitate handling and to resist squeezing pressure from the infant's hands (not shown). A plurality of measurement lines 22 are provided about the peripheral surface of the main body portion 11 and nipple section 12. Measurement markings or indicia 23 may also be provided to facilitate the accurate measurement of the liquid medication and/or nutrient within dispenser 10. The measurement lines 22 and indicia may be integrally formed in the molding process. In accordance with another feature of the invention, metric and English measurement indicia 23, 24 are provided to facilitate the mixing of a dosage of a liquid medicament with a desired flavorful liquid such as juice or to enable the mixing of a desired liquid formulation. In this manner, a dispenser 10 is provided having greater flexibility of use and enabling improved medicament and nutrient dosage delivery than heretofore possible.

In accordance with the present preferred embodiment, the main body portion 11 is formed in a molding process to include an upper annular flange 13. Flange 13 is affixed in any conventional manner, for example, epoxy glued to the lower surface 26 of the mouth guard 14 to form a fluid-tight seal therebetween.

Mouth guard 14 may be formed of any suitable material such as a rigid plastic. Mouth guard 14 is integrally formed to have a pipe shaped upwardly projecting cap mounting member 30. Cap mounting member 30 includes a plurality of circumferential male threads 31 and a central hole or aperture 32 which extends through mouth guard 14. Aperture 32 is medially located on the circular or oval shaped mouth guard disc 14 for being in alignment with cavity mouth opening 18. The diameter or size of cap mounting member 30 and aperture 32 are predetermined to facilitate easy pouring/filling of liquid medicament, nutrient fluids and other liquids into aperture 32 and, thereby, to fill the nipple 12 and main body portion 11 with the liquid formulation to a selected measurement.

It should be recognized at this time, that in contrast to the prior art, a substantially precise formulation may be achieved by first filling the nipple 12 to the graduated metric measurement level and then adding a liquid transfer fluid such as juice or other medicinal to a desired formulation. With cap 15 and air valve member 16 in closed position, the formulation may be mixed simply by turning dispenser 10 upside down.

An air valve member 16 is provided to enable the controlled flow of air into cavity 40 and, thereby, substantially control the rate of fluid flow from nipple opening 17. In this manner, the oral administration of medicament or nutrient formulation may be dispensed to the infant, toddler or patient at a slow to fast rate of flow.

Although it is recognized that various valve means may be designed, it is a feature of the present invention to utilize a valve member 16 to enable selective adjustment of the medicament flow-rate from an infant's bottle or pacifier.

One preferred embodiment of valve member 16 consists of a cap 41 having female internal threads 42 designed to matingly engage with the male threads 43 located on cap nipple 44. Cap nipple 44 may be integrally formed with cap 15. A plurality of holes or apertures 45 are provided in cap nipple 44, which communicates into reservoir chamber 40.

Cap 15 comprises a generally round bottle like cap shape and having internal female threads 46 designed to mate with the male threads 31 on cap mounting member 30.

Thus, important features of the present invention are to provide an oral medicament dispenser 10 having means for measuring the formulations of medicament and other liquids and to dispense such formulation at a relatively controllable fluid flow rate.

For example, with tightly screwing cap 41 down onto cap nipple 44, and thereby sealing all the nipple air ports 45, a vacuum air lock is established to retard, reduce or virtually cease any liquid flow from the nipple 12 hole 17.

Figure 3:
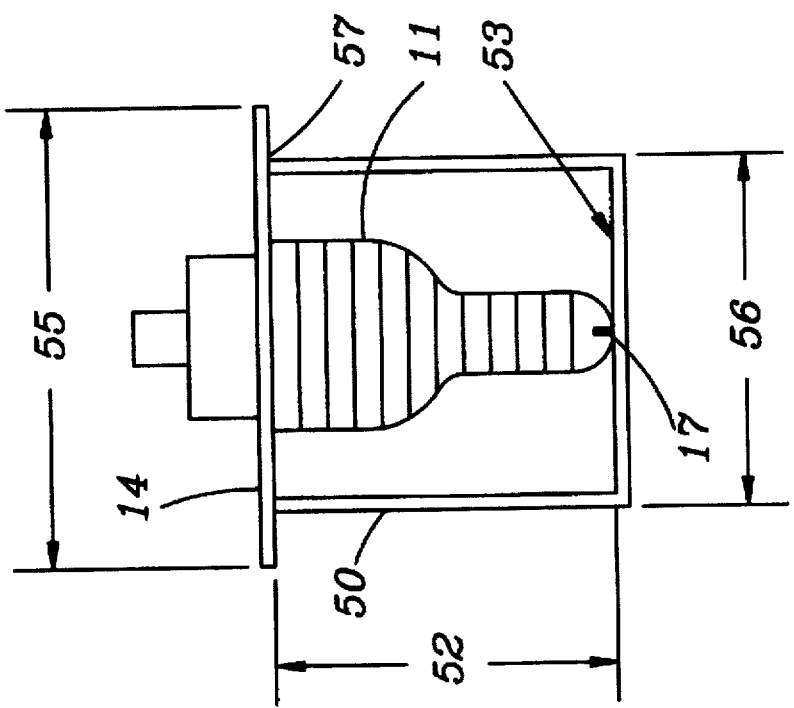
FIG. 3 is a side view of the dispenser placed in a holder in accordance with one feature of the present invention.

With reference now to FIG. 3, another important feature of the present invention will now be described.

Typically, infant bottles or pacifiers are simply placed on a counter top or other surface which may be unclean. It is noted that from time to time, during the administration of a medicament, the dispensing must be interrupted to perform other functions such as, for example, changing of a diaper or burping of an infant. During such interruptions, the dispenser heretofore was placed on its side on a bed or counter top or other surface which may result in leaking of the medicament formulation from the dispenser.

Figure 4:
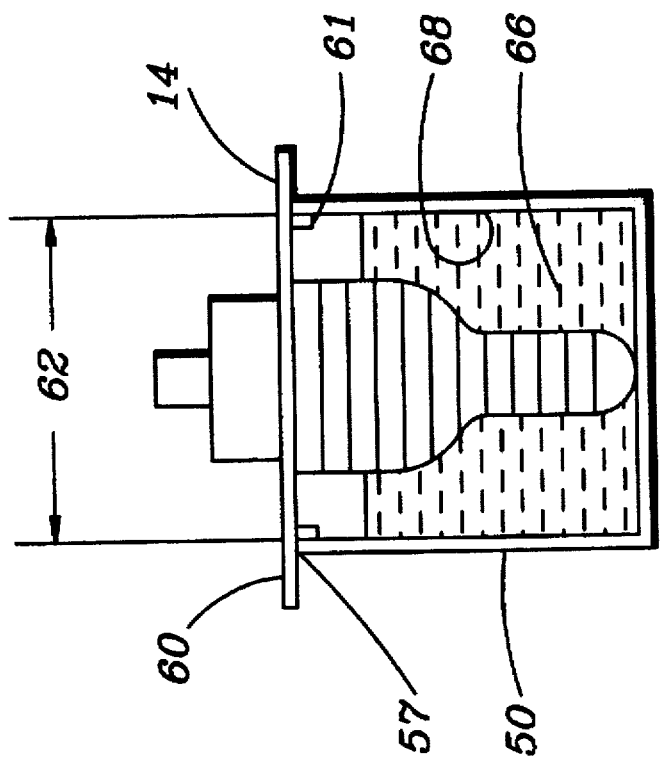
FIG. 4 is a side view of the dispenser being partially submerged in a fluid within the holder in accordance with another feature of the present invention.

In accordance with the present dispenser system invention, a holder or container 50 is provided for temporary and longer term storage of dispenser 10. In the preferred embodiment, holder 50 comprises a glass or plastic container having a jar shape. The dimensions of holder 50 are predetermined to enable the up-right vertical mounting of dispenser 10 as illustrated in FIGS. 3 and 4. The height 52 of holder 50 and the length of the body portion 11 and nipple 12 are selected such that the tip of nipple 12 abuts the bottom surface 53 of holder 50 and, thereby, provides a means of closing or plugging nipple hole or aperture 17. Nipple 12 as noted above is formed of a flexible rubber or latex material which deforms slightly when compressed against bottom wall 53 to urge aperture 17 to close. In this manner, the medicament formulation is substantially maintained within dispenser 10 during such periods of temporary interruption of feeding of the infant or patient.

The diameter dimension 55 of mouth guard 14 is designed to extend beyond the upper rim 57 of holder 50. Accordingly, the diameter 56 of holder 50 is less than the diameter 55 of mouth guard 14.

Holder 50 is preferably transparent to facilitate the care taker's observation of the liquid formulation level within dispenser 10. Another beneficial advantage and feature of the present system is that if any leakage does occur from dispenser 10, such leaked fluid is captured within holder 50 and can be reintroduced back into dispenser 10. In this manner, expensive medications are not lost and more precise dosage amounts may be delivered to the infant or patient.

With reference now to FIG. 4, an alternative embodiment of a mouth guard disc 60 and its cooperation with holder 50 to effect a more positive closure therebetween is depicted. Basically speaking, mouth guard 60 is similar to mouth guard 14 with the exception of a sealing/locking circular O-ring 61. O-ring 61 may be formed of any suitable material such as a flexible plastic, rubber or caulk like material. O-ring 61 is designed to have an outer diameter 62 equal to or slightly greater than the inner diameter of holder 50 such that a force fit or snug fit may be established between O-ring 61 and holder 51. In this manner, dispenser 10 may be securely maintained in holder 50 until manually removed by a person for intended use.

An advantageous feature of this embodiment contemplates the use of a warming and/or sterilization fluid 66 in holder 50. It should also be recognized that with the warming/sterilizing solution being maintained at or slightly below the level of the formulation in holder 10, a further hydraulic effect is created to virtually eliminate outflow of the formulation from outlet aperture 17.

With O-ring 61 snugly abutting against the side walls 68 of holder 50, spillage by accidental knocking over of holder 50 is substantially eliminated.

Figure 5:
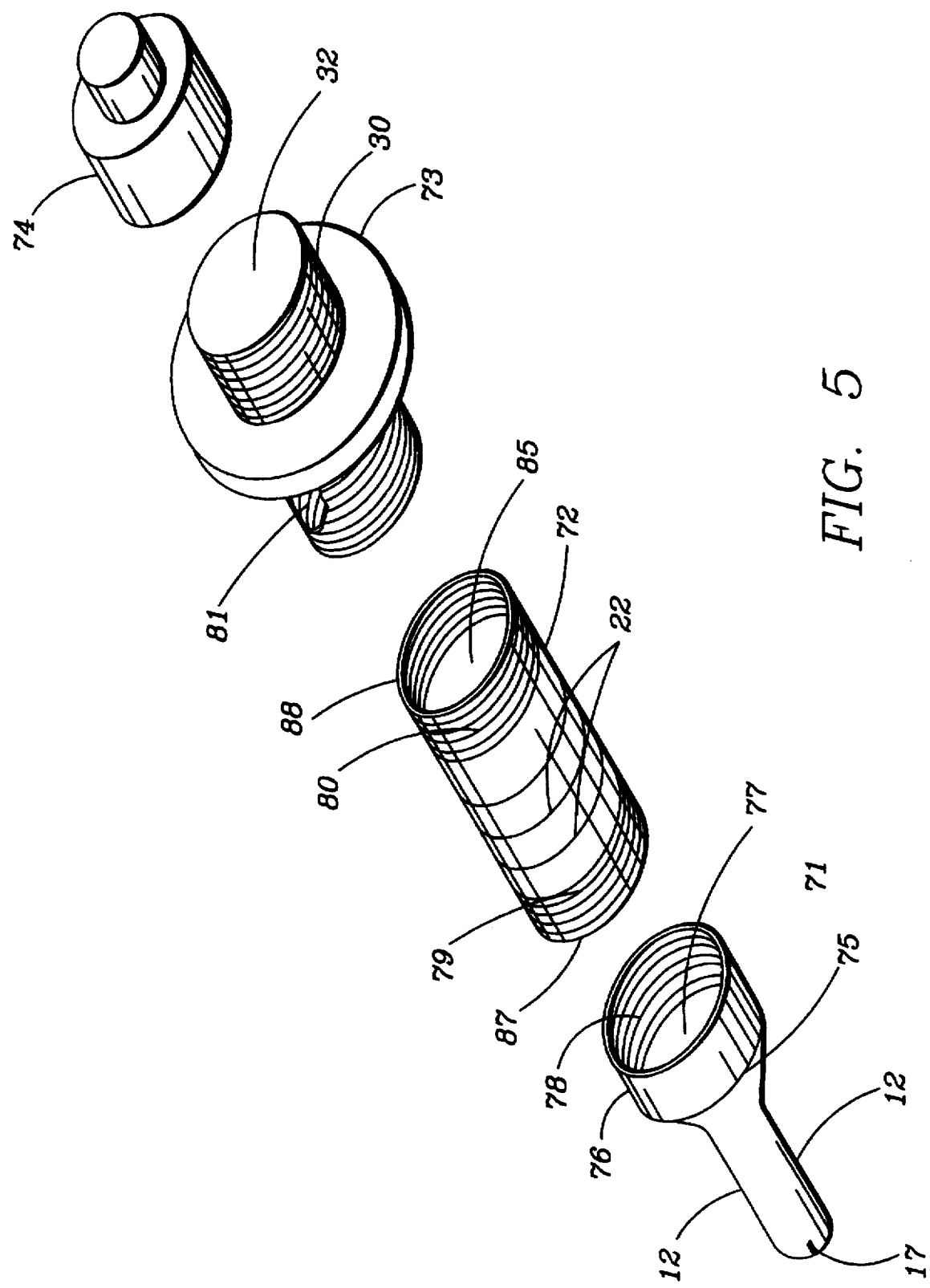
FIG. 5 is an exploded view of an alternative embodiment of the dispenser unit in accordance with the present invention.

With reference now to FIG. 5, an alternative embodiment of a dispenser in accordance with the present invention will now be described.

Basically speaking, the dispenser comprises a nipple member 71, a tubular body member 72, a mounting unit 73 and a cap member 74. Nipple member 71 includes a flexible rubber like nipple 12 having an outlet fluid port or hole 17. The upper circumferential ridge 75 is affixed and fluid-tight sealed to a lower cap member 76. Lower cap member 76 may be formed of any suitable material such as plastic. Cap member 76 has a cavity 77 which communicates with nipple reservoir chamber 40. A plurality of female threads 78 are provided for mating with male threads 79 found on body member 72.

Tubular body member 72 may be formed of any suitable material such as plastic or glass and includes a plurality of measurement lines or markings 22. A plurality of male threads 80 are provided at the top end of tubular body member 72 for matingly screw engagement with female threads 81 located about the inner circumferential wall of mounting unit 73. Mounting unit 73 also includes a mounting disc 14 and an upper tubular shaped cap mounting and liquid inlet port member 30. Inlet port member 30 includes a plurality of male threads designed for mating engagement with female threads of cap 74.

Cap 74 may also include an air inlet valve means to regulate the liquid dispensing flow rate from outlet port 17 of nipple 12. As with the dispenser 10 described above, cap 74 may be removed for filling the nipple 12 and body member 72 to the desired medicament and nutrient formulation desired.

It should now be recognized that the present invention incorporates several structural and functional advantageous features, such as, but not limited to:

a medicament/nutrient dispenser and holder system;

a medicament dispenser having measurement indicia;

a dispenser having means for regulating flow rate;

a dispenser type pacifier having a dual function mouthguard and mounting platform;

a holder means for holding and retarding outlet flow/leaking from a nipple during storage;

a holder means for heating the dispenser formulation.

a liquid dispensing system having a holder means to facilitate the filling of a dispenser device with a medicament/nutrient formulation and to substantially eliminate leakage and loss of such formulation from the nipple aperture/hole during such filling or formulation process. In this manner the prior art long recognized but heretofore not solved problem of leakage/loss/fluid dripping from the nipple during the filling process is substantially eliminated. Such leakage/loss/fluid dripping was a substantial problem because it represented an unmeasured loss of a medication which may require very precise dosage to be effective.

It should be recognized that the synergistic structural and functional advantageous features of the present invention as highlighted above are distinguishing features of the invention which are incorporated into the claims without specifically being stated therein.

Figure 6:
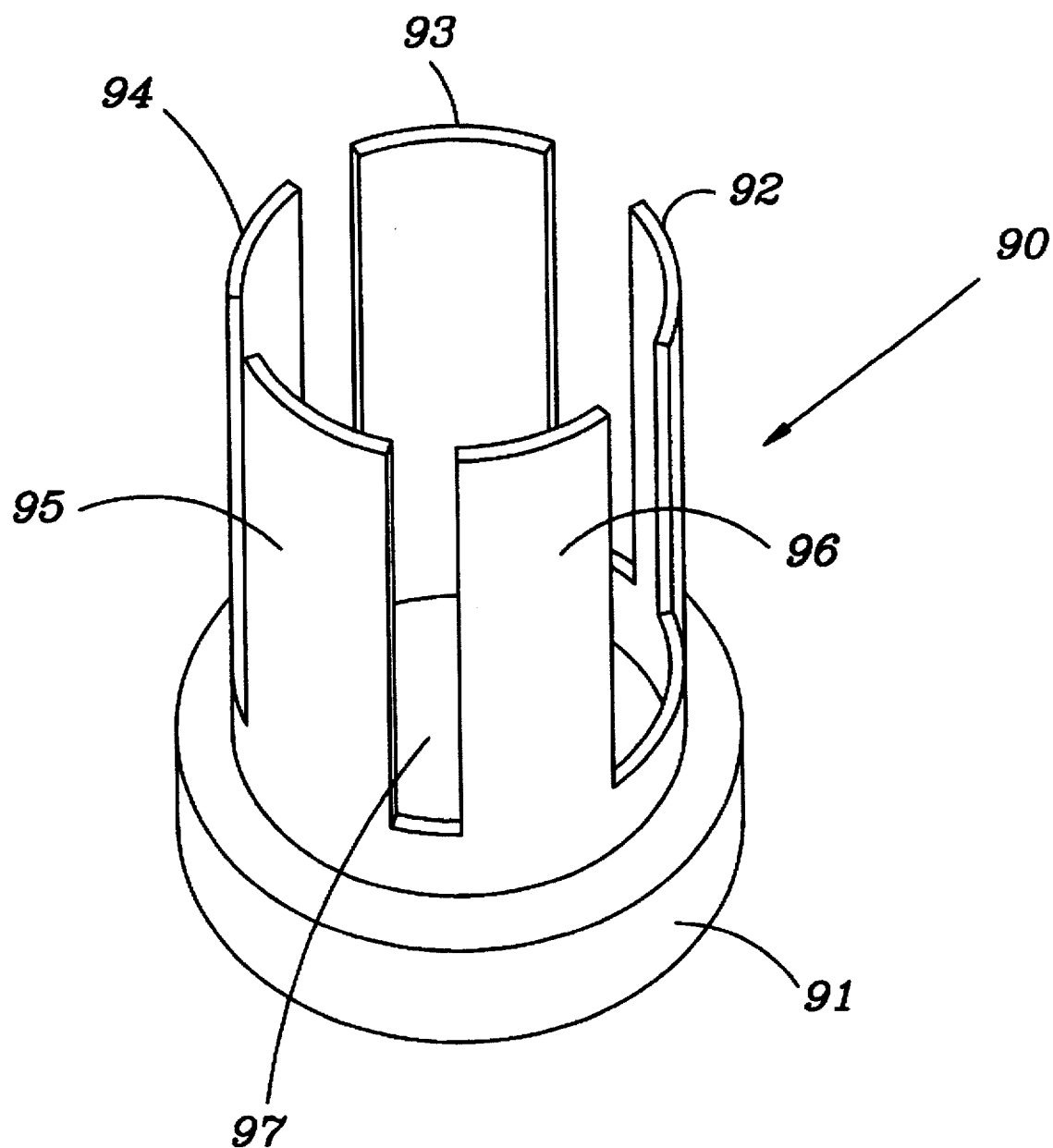
FIG. 6 is a perspective view of an alternative liquid dispenser in accordance with the present invention.

With reference now to FIG. 6, an alternative embodiment 90 of holder 50 will now be described. Basically speaking, holder 90 comprises a base unit comprising a base member 91 having a bottom floor section 97 and a plurality of, for example, five, upwardly projecting and spaced apart column like members 92–96. Holder 90 functions in similar manner to holder 50 illustrated in FIG. 3, with the exception that holder 90 is not used to contain a warming fluid 66 as demonstrated in FIG. 4. The mounting disc 14 is dimensioned to fit atop of the columns 92–96 so as to mount the dispenser 10 in a stand-up position similar to that illustrated in FIG. 3.

While there has been shown and described what is considered to be the preferred embodiments of the invention, it is desired to secure in the appended claims all modifications as fall within the true spirit and scope of the invention.

I claim:

1. A liquid medication, nutrient and fluid measuring and dispensing system having particular utility for pediatric and infant care, in combination, comprising:

a dispenser device (10) consisting of a fluid reservoir means defining a fluid reservoir (40) and having measurement indicia (22,23) for enabling formulation of at least one fluid to a selected quantity, and a nipple means (12) connected to and in communication with a lower end of said fluid reservoir means for receiving fluid therefrom, and having a fluid outlet port (17), and a dual function mouth guard and dispenser mounting disc (14,73) affixed in fluid-tight communication with said fluid reservoir means and having wall portions defining a fluid passage opening into said fluid reservoir (40), and having a male threaded neck member (30) with wall portions defining a fluid inlet port (32) communicating said fluid passageway opening for enabling the liquid medication, nutrient and fluids to be poured into said fluid reservoir means, and a cap means (15) having female threaded inner wall portions for being screwed onto said male threaded neck member;

valve means (16) operatively connected to said neck member (30) for controlling the rate of fluid flow from said fluid outlet port (17);

holder means (50) having a base member (53) for providing stable support and for engaging with a portion of said nipple chamber means for effecting a plug of said fluid outlet port (17) with said dispenser (10) being mounted within said holder means to thereby substantially stop any fluid leakage from said fluid outlet port, and having wall portions (57) for mounting supporting said dual function mouthguard and mounting disc (14, 73).

2. A dispensing system as in claim 1, wherein:
the fluid reservoir comprises the unitary fluid reservoir means (11) and the nipple means (12) and having a plurality of measurement indicia (22,24) provided on said unitary fluid reservoir.

3. A dispensing system as in claim 2, wherein:
the fluid reservoir means being formed of a transparent material.

4. A dispensing system as in claim 2, wherein:
the fluid reservoir means being formed of a resin material and being translucent with said measurement indicia being visually identifiable for measuring fluid levels within said fluid reservoir means.

5. A dispensing system as in claim 1, wherein:
the dual function mouth guard and dispenser mounting disc being formed of a plastic material.

6. A dispensing system as in claim 1, wherein:
the neck member (30) being dimensioned and shaped to function as a funnel means for facilitating pouring of liquids therein.

7. A dispensing system as in claim 1, wherein:
the cap means being formed of a plastic.

8. A dispensing system as in claim 1, wherein:
the valve means (16) comprises an adjustable air inlet port.

9. A dispensing system as in claim 1, wherein:
the valve means comprises a nipple shaped section projecting upwardly from said cap means, and having wall portions defining at least one aperture communicating with the fluid reservoir chamber (40), and having a cap for selectively adjusting the aperture whereby an alterable air passageway being effected so as to control air flow into said fluid reservoir chamber and thereby affect a selectable fluid flow rate form fluid outlet port (17).

10. A dispensing system as in claim 1, wherein:
the holder means being formed of a resin material.

11. A dispensing system as in claim 1, wherein:
the holder means being formed of a glass material.

12. A liquid medication, nutrient and fluid measuring and infant pacifier and dispensing system, in combination, comprising:
a pacifier and dispenser device consisting of a fluid reservoir means (71,72) having wall portions defining a fluid reservoir (77,85) and a nipple chamber means (12) and a plurality of measurement indicia (22,23,24) provided on said fluid reservoir means for enabling formulation of a fluid(s) to selected quantities, said nipple chamber means (12) being integrally formed with and in communication with a lower end of said fluid reservoir means for receiving fluid therefrom, and having a fluid outlet port (17), said fluid reservoir means being formed of a material for enabling said measurement indicia being visually identifiable with fluid levels within said fluid reservoir means, and a dual function mouth guard and dispenser mounting disc (14,73) affixed in fluid-tight communication with said fluid reservoir means and having wall portions defining a fluid passageway opening into said fluid reservoir (40) and a neck member (30) being dimensioned and shaped to function as a funnel means for facilitating pouring of liquids therein and having a plurality of male threads, said neck member defining a fluid inlet port (32) communicating with said fluid passageway opening for enabling the liquid medication, nutrient and fluids to be poured into said fluid reservoir means, and a cap means (15) having female threaded inner wall portions for being screwed onto said male threaded neck member;

valve means (16) for controlling the rate of fluid flow from said nipple outlet port (17), said valve means comprises a nipple shaped section projecting upwardly from said cap means, and having wall portions defining at least one aperture communicating with the fluid reservoir chamber (40), and having a cap for selectively adjusting the aperture whereby an alterable air passageway being effected so as to control air flow into said fluid reservoir chamber and thereby affect a selectable fluid flow rate from said fluid outlet port (17)

holder means (50,90) having a base member (53,91) for providing stable support and for engaging with a portion of said nipple chamber means for effecting a plug of said fluid outlet port (17) with said dispenser (10) being mounted within said holder means to thereby substantially stop any fluid leakage from said fluid outlet port, and having wall portions (57, 92–96) for mounting supporting said dual function mouth guard and mounting disc (14,73);

whereby a synergism being effected of a combination of structural and functional features of:
a medicament/nutrient dispenser and holder system;
a medicament dispenser having measurement indicia;
a dispenser having means for regulating flow rate;
a dispenser type pacifier having a dual function mouthguard and mounting platform;
a holder means for holding and retarding outlet flow/leaking from a nipple during storage;
a holder means for heating the dispenser formulation;
a liquid dispensing system having a holder means to facilitate the filling of a dispenser device with a medicament/nutrient formulation and to substantially eliminate leakage and loss of such formulation from the nipple aperture/hole during such filling or formulation process.

13. A liquid medication, nutrient and fluid measuring and infant pacifier and dispensing system as in claim 12, wherein:
said pacifier and dispenser device comprises a discrete nipple member (71), a discrete tubular body member (72), a discrete mounting unit (73) and a cap member (74), said nipple member includes a flexible nipple having said outlet fluid port, an upper circumferential ridge (75) is affixed and fluid-tight sealed to a lower cap member (76), said lower cap member being formed of plastic, said lower cap member having wall portions defining a lower fluid reservoir (77) which communicates with an upper fluid reservoir (88), and a plurality of female threads (78) are provided for mating with male threads (79) on body member (72).

14. A liquid medication, nutrient and fluid measuring and infant pacifier and dispensing system as in claim 13, wherein:
said tubular body member (72) being formed of a transparent material and includes a plurality of measurement lines (22) and measurement indicia (23,24), and having a plurality of male threads (80) provided at a top end of said tubular body member for mating screw engagement with a plurality of female threads (81) located about the inner circumferential wall of said mounting unit (73).

* * * * *